United States Patent [19]

Krausz

[11] 4,104,383
[45] Aug. 1, 1978

[54] DERIVATIVES OF PHENYLPROPENYLAMINE

[75] Inventor: François Krausz, Montpellier, France

[73] Assignee: C M Industries, Paris Cedex, France

[21] Appl. No.: 692,787

[22] Filed: Jun. 4, 1976

Related U.S. Application Data

[63] Continuation of Ser. No. 519,752, Oct. 31, 1974, abandoned.

[30] Foreign Application Priority Data

Nov. 2, 1973 [GB] United Kingdom ............ 51123/73

[51] Int. Cl.² ............ A61K 31/395; A61K 31/135
[52] U.S. Cl. ............ 424/248.4; 260/239 B;
260/293.72; 260/326.87; 260/570.5 R;
260/570.5 CA; 424/274; 424/330; 424/246;
424/267; 424/250; 424/244; 542/429; 542/431;
542/469; 542/470; 544/59; 544/178; 544/106;
544/403
[58] Field of Search ............ 260/240 K, 247, 293.72,
260/570.5 TC, 570.5 CA; 424/248.4, 274, 330,
246, 267, 250; 542/469

[56] References Cited

U.S. PATENT DOCUMENTS

| 3,485,873 | 12/1969 | Aceto et al. | 424/330 |
|---|---|---|---|
| 3,573,291 | 3/1971 | Fauran et al. | 260/240 K |
| 3,625,965 | 12/1971 | Irikura | 260/240 K |

OTHER PUBLICATIONS

Foldeak et al., Acta Univ. Szeged 10 (1964), pp. 41–56.
Goldschmidt et al., Rec Trav. Chim 69 (1930), pp. 1109–1117.
Bennington et al., J. Org Chem 23 (1958), pp. 1979–1984.
Goldschmidt, Chem Abst. 43 (1949) 5156 f.

Primary Examiner—Arthur P. Demers
Attorney, Agent, or Firm—Bacon & Thomas

[57] ABSTRACT

Compounds having psychostimulant, antispasmodic, hypotensive and analgesic properties are disclosed. The compounds have the formula:

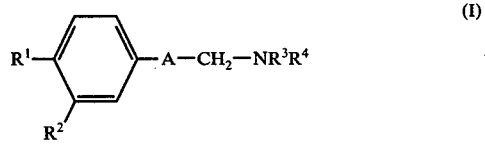

(I)

in which
R² is selected from the group consisting of a hydrogen atom and a halogen atom;
R¹ is selected from the group consisting of a cyclohexyl group and a phenyl group, and is a cyclohexyl group when R² is a halogen atom;
A is selected from the group consisting of $CH_2CH_2$ and $CH=CH$ groups; and
$NR^3R^4$ is selected from the group consisting of an alkylamino group, a dialkylamino group and a heterocyclic ring containing from 5 to 7 atoms in the ring, said ring optionally having one or more sbustituents and optionally containing a second heteroatom; and acid addition salts of said compounds.

12 Claims, No Drawings

DERIVATIVES OF PHENYLPROPENYLAMINE

This is a continuation of application Ser. No. 519,752, filed Oct. 31, 1974, now abandoned.

The present invention relates to certain new derivatives of phenylpropylamine, to a process for their preparation and to the use of these derivatives in pharmaceutical compositions.

Thus, the present invention consists in compounds of general formula (I):

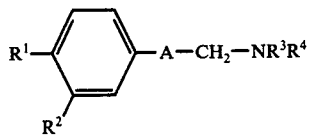

(I)

in which $R^2$ is a hydrogen or halogen (fluorine, chlorine, bromine or iodine, preferably chlorine) atom; $R^1$ is a phenyl or cyclohexyl group, and is a cyclohexyl group when $R^2$ is a halogen atom; A is a $CH_2CH_2$ or $CH=CH$ group; and $R^3$ and $R^4$, which may be the same or different are each a hydrogen atom or an alkyl group, preferably having from 1 to 3 carbon atoms, provided that $R^3$ and $R^4$ may not both be hydrogen atoms, or $NR^3R^4$ may represent a substituted or unsubstituted heterocyclic group having from 5 to 7 atoms in the heterocyclic ring and optionally containing a second hetero atom; and acid addition salts of said compounds.

According to one embodiment of the invention, when $NR^3R^4$ is a heterocyclic group, it may be unsubstituted or may have one or more substituents, preferably $C_1-C_5$ alkyl groups or hydroxyalkyl groups having from 1 to 5 carbon atoms. Examples of such heterocyclic groups are: pyrrolidino; morpholino; thiomorpholino; 2,6-dimethylmorpholino; piperidino; 4-methylpiperidino; piperazino; 4-(β-hydroxyethyl)-piperazino; 4-methylpiperazino; and azepino groups.

The acid addition salts of the present invention may be prepared by mixing a compound of general formula (I) with an organic or inorganic acid; preferred acids are hydrochloric acid, hydrobromic acid, hydroiodic acid, oxalic acid, succinic acid, maleic acid, fumaric acid, acetic acid, benzoic acid, citric acid, lactic acid, malic acid, ascorbic acid, salicyclic acid, glutamic acid, methanesulphonic acid and p-toluenesulphonic acid.

The compounds of formula (I) may be prepared by condensing an acetophenone of general formula (II):

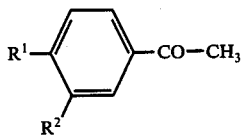

(II)

(in which $R^1$ and $R^2$ are as defined above) in a Mannich reaction with formaldehyde and a primary or secondary amine, reducing the amino-ketone thus formed to a 3-amino-1-phenyl-propan-1-ol, and subsequently dehydrating this 3-amino-1-phenyl-propan-1-ol. The compound so produced is of general formula (I) in which A is $CH=CH$; subsequently, if desired, this compound may be hydrogenated to produce a compound of formula (I) in which A is $CH_2CH_2$.

Thus, the present invention further consists in a process for the preparation of a compound of formula (I) (as hereinbefore defined, which comprises the steps of:

(a) condensing an acetophenone of formula (II) (as hereinbefore defined) with formaldehyde and an amine of formula $HNR^3R^4$ ($R^3$ and $R^4$ being as defined above) to form an amino-ketone;

(b) reducing said amino-ketone to a corresponding 3-amino-1-phenyl-propan-1-ol;

(c) dehydrating said 3-amino-1-phenyl-propan-1-ol to a compound of formula (I) in which A is $CH=CH$; and if desired (d) hydrogenating said compound of formula (I) in which A is $CH=CH$ to form a compound of formula (I) in which A is $CH_2CH_2$. The compound of formula (I) so produced may then be reacted with an acid to form the acid addition salt.

In step (b) of the process, the reduction is preferably effected by means of a hydride reducing agent, preferably at a temperature below 10° C and preferably in the presence of an alcohol. Examples of hydride reducing agents are sodium borohydride, lithium borohydride, lithium aluminium hydride, and potassium borohydride, sodium borohydride being the preferred reducing agent.

In step (c) of the process of the invention, the dehydration is preferably effected by means of a dehydrating agent such as p-toluenesulphonic acid. According to a preferred embodiment of the invention, the dehydration is carried out by heating the 3-aminopropan-1-ol with p-toluenesulphonic acid in toluene at the reflux temperature of the reaction medium, continuously withdrawing water, until the reaction is substantially complete, which normally requires approximately 20 hours.

The hydrogenation of step (d), if required, may be carried out using a conventional hydrogenation catalyst, such as platinum oxide.

The sequence of reactions employed in the process of the present invention is as follows:

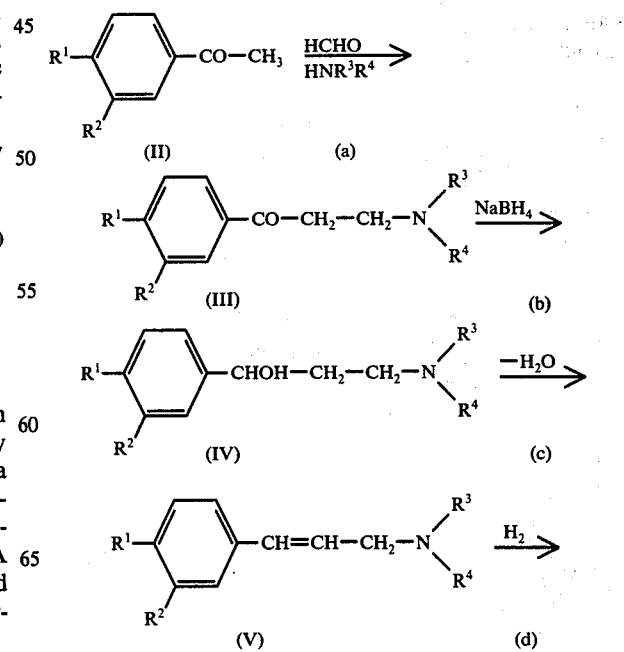

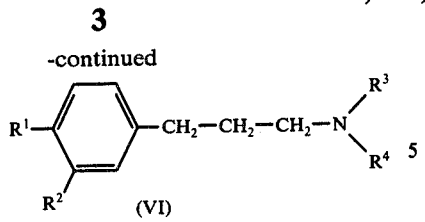

(VI)

The process of the invention is further illustrated with reference to the following Examples.

EXAMPLE 1

3-Chloro-4-cyclohexyl-1-(3-diethylamino-propen-1-yl)-benzene (a) 54 g of diethylamine hydrochloride, 100 g of 3-chloro-4-cyclohexyl-acetophenone and 15.1 g of paraformaldehyde in 75 ml of absolute ethanol were heated under reflux for 4 hours in the presence of 1.5 ml of 10 N hydrochloric acid. When the reaction was complete, the solvent was evaporated over a water bath under the vacuum produced by a water-jet pump, and the residue was then recrystallized from acetone. 116 g (a yield of 76.5% of theory) of 3-chloro-4-cyclohexyl-1-(3-diethylamino-1-oxo-propyl)-benzene were obtained; the product had a melting point of 156°–158° C (with decomposition).

(b) 116 g of the product of step (a) were suspended in a mixture of 1 liter of methanol and 60 ml of 40% sodium carbonate. 40 g of sodium borohydrate were then added slowly to this suspension, maintaining the temperature below 8° C. After all of the sodium borohydrate had been added, the mixture was left for 12 hours at ambient temperature, after which 1.5 liters of 5% soda solution were added and the mixture was extracted with 700 ml of isopropyl ether. The organic phase was washed with water, dried over sodium sulphate and then evaporated to dryness. 81 g (yield 77% of theory) of 3-chloro-4-cyclohexyl-1-(3-diethylamino-1-hydroxy-propyl)-benzene were obtained in the form of a yellow oil.

(c) 81 g of the compound produced in step (b) were dissolved in 500 ml of toluene and, to the solution so produced, was added a solution of 76 g of p-toluenesulphonic acid in the minimum quantity of water. The mixture was heated under reflux for about 20 hours, continuously removing the water formed. At the end of this time, the solution was cooled and poured into 2 liters of water, to which ammonia was added until the solution became alkaline. The organic phase was then separated, washed with water and dried with sodium sulphate. 66 g (yield 86%) of 3-chloro-4-cyclohexyl-1-(3-diethylamino-propen-1-yl)-benzene (hereinafter referred to as compound 933 CB) were obtained in the form of a light brown oil. This was dissolved in ether and reacted with a sufficient quantity of hydrochloric acid dissolved in the same solvent to produce 67 g of the hydrochloride having a melting point of 161° C.

EXAMPLE 2

3-Chloro-4-cyclohexyl-1-(3-dimethylamino-propen-1-yl)-benzene (a) The process was the same as described in step (a) of Example 1, except that an equimolar quantity of dimethylamine hydrochloride was used in place of the diethylamine hydrochloride. The hydrochloride of 3-chloro-4-cyclohexyl-1-(3-dimethylamino-1-oxo-propyl)-benzene was obtained in a yield of 78% and had a melting point of 186°–188° C (with decomposition).

(b) Following the method described in step (b) of Example 1, the compound prepared in step (a) of this Example was used to produce 3-chloro-4-cyclohexyl-1-(3-dimethylamino-1-hydroxypropyl)-benzene in a yield of 90%; the product was a brown oil.

(c) From the compound produced in step (b) and following the method described in step (c) of Example 1, 3-chloro-4-cyclohexyl-1-(3-dimethylamino-propen-1-yl)-benzene was obtained in a yield of 80%; this compound is hereinafter referred to by the reference "31004 CB". Following the procedure described in Example 1, the hydrochloride of this compound was obtained quantitatively and was found to have a melting point of 163°–164° C.

EXAMPLE 3

3-Chloro-4-cyclohexyl-1-(3-morpholino-propen-1-yl)-benzene (a) Following the procedure described in step (a) of Example 1, except that diethylamine hydrochloride was replaced by an equimolar quantity of morpholine hydrochloride, the hydrochloride of 3-chloro-4-cyclohexyl-1-(3-morpholino-1-oxo-propyl)-benzene was obtained in a yield of 73%; the melting point of this compound was 192°–193° C.

(b) This compound was then used in the process described in step (b) of Example 1 to produce 3-chloro-4-cyclohexyl-1-(3-morpholino-1-hydroxy-propyl)-benzene in the form of a yellow oil and in a yield of 86%.

(c) Following the process described in step (c) of Example 1, the compound prepared in step (b) was then used to produce 3-chloro-4-cyclohexyl-1-(3-morpholino-propen-1-yl)-benzene in the form of a yellowish oil and in a yield of 88%; this compound is hereinafter referred to by the reference "31013 CB". The hydrochloride of compound 31013 CB was prepared as described previously, in a yield of 95%, and was found to have a melting point of 198°–200° C.

EXAMPLE 4

3-Chloro-4-cyclohexyl-1-(3-pyrrolidino-propen-1-yl)-benzene (a) The process described in step (a) of Example 1 was repeated, except that the diethylamine hydrochloride was replaced by an equimolar amount of pyrrolidine hydrochloride to produce the hydrochloride of 3-chloro-4-cyclohexyl-1-(3-pyrrolidine-1-oxopropyl)-benzene in a yield of 73%. This compound had a melting point of 180°–190° C (with decomposition).

(b) Following the process described above in step (b) of Example 1, the compound prepared in step (a) above was used to produce 3-chloro-4-cyclohexyl-1-(1-hydroxy-3-pyrrolidino-propyl)-benzene in a yield of 91%. The compound had a melting point of 90° C.

(c) This compound was then used in the process described in step (c) of Example 1 to produce 3-chloro-4-cyclohexyl-1-(3-morpholino-propen-1-yl)-benzene (referred to by the code "31015 CB") in a yield of 87%; from this the hydrochloride was prepared as described above and was found to have a melting point of 161°–162° C.

EXAMPLE 5

4-(3-Diethylamino-propen-1-yl)-biphenyl (a) 50 g of biphenyl methyl ketone, 10 g of paraformaldehyde and 30 g of diethylamine hydrochloride were heated under reflux for 6 hours in 200 ml of absolute ethanol and in the presence of 1 ml of 10 N hydrochloric acid. On cooling, a mixture of the reaction product in the form of its hydrochloride and of the initial ketone crystallized from the reaction mixture. These were separated by treating the mixture with 500 ml of 10% hydrochloric acid and the aqueous solution was extracted with ethyl acetate. The organic phase was disposed of and the aqueous phase was made alkaline by the addition of 10 N aqueous soda. The liberated base was finally extracted with ether. After drying the ethereal solution with sodium sulphate and evaporating the ether, 4-(3-diethylamino-1-oxo-propyl)-biphenyl was obtained in the form of a yellow oil and in a yield of 55%.

(b) This 4-(3-diethylamino-1-oxo-propyl)-biphenyl was then used in the process described in step (b) of Example 1 to produce 4-(3-diethylamino-1-hydroxy-propyl)-biphenyl in the form of a brown oil (yield 87%).

(c) This compound was then converted to 4-(3-diethylamino-propen-1-yl)-biphenyl (compound "994 CB") following the method described in step (c) of Example 1. The compound was obtained in a yield of 88% and was found to have a melting point of 60° C. The hydrochloride was then prepared in ether and was found to have a melting point of 210°–212° C; it was obtained in a yield of 87%.

EXAMPLE 6

4-(3-diethylamino-propyl)-biphenyl

The hydrochloride of 4-(3-diethylamino-propen-1-yl)-biphenyl prepared in Example 5 was reduced in 10 volumes of ethanol and in the presence of 1% (based on the weight of compound reduced) of platinum oxide, using hydrogen at ambient pressure. After absorption of hydrogen had ceased, the catalyst was separated, the alcohol evaporated and the residue recovered in anhydrous ether. The hydrochloride of 4-(3-diethylamino-propyl)-biphenyl (compound "31001 CB") was obtained in a yield of 77%; its melting point was 140° C.

EXAMPLE 7

3-Chloro-4-cyclohexyl-1-(3-diethylamino-propyl)-benzene

This compound (reference "934 CB") was obtained in the form of its hydrochloride in a yield of 83% after recrystallization from ether, using the process described in Example 6 and starting from the hydrochloride of compound 933 CB (prepared in Example 1). The hydrochloride had a melting point of 134° C.

EXAMPLE 8

3-Chloro-4-cyclohexyl-1-(3-dimethylamino-propyl)-benzene

Starting from the hydrochloride of compound 31004 CB (Example 2) and using the method described in Example 6, the hydrochloride of 3-chloro-4-cyclohexyl-1-(3-diethylamino-propyl)-benzene (compound "31012 CB") was obtained in a yield of 86% after recrystallization from ether; the hydrochloride had a melting point of 190°–191° C.

EXAMPLE 9

3-Chloro-4-cyclohexyl-1-(3-pyrrolidino-propyl)-benzene

The hydrochloride of this compound (compound "31016 CB") was obtained using the process of Example 6 and starting from the hydrochloride of compound 31015 CB (Example 4). After recrystallization from ether, the yield was 53% and the melting point of the hydrochloride was 175°–177° C.

EXAMPLE 10

4-Cyclohexyl-1-(3-diethylamino-propen-1-yl)-benzene

Following the procedure described in steps (a) to (c) Example 1, except that 3-chloro-4-cyclohexyl acetophenone was replaced by an equimolar quantity of 4-cyclohexyl acetophenone, the hydrochloride of 4-cyclohexyl-1-(3-diethylamino-propen-1-yl)-benzene (compound "31023 CB") was obtained after recrystallization from ether; the hydrochloride had a melting point of 171°–172° C.

EXAMPLE 11

3-Fluoro-4-cyclohexyl-1-(3-diethylamino-propen-1-yl)-benzene

Following the procedure described in steps (a) to (c) of Example 1, except that 3-chloro-4-cyclohexyl acetophenone was replaced by an equimolar quantity of 3-fluoro-4-cyclohexyl acetophenone, the hydrochloride of 3-fluoro-4-cyclohexyl-1-(3-diethylamino-propen-1-yl)-benzene was obtained after recrystallization from ether. The hydrochloride had a melting point of 171°–172° C.

The following Table 1 summarizes the product obtained in Examples 1 to 11:

TABLE I

| Ex. No. | Code No. | $R_1$ | $R_2$ | A | $-NR_3R_4$ | Melting point of hydrochloride (° C) |
|---|---|---|---|---|---|---|
| 1 | 933 CB | cyclohexyl | Cl | CH=CH | $-N(C_2H_5)_2$ | 161 |
| 2 | 31,004 CB | cyclohexyl | Cl | CH=CH | $-N(CH_3)_2$ | 163–164 |
| 3 | 31,013 CB | cyclohexyl | Cl | CH=CH | morpholino | 198–200 |
| 4 | 31,015 CB | cyclohexyl | Cl | CH=CH | pyrrolidino | 161–162 |
| 5 | 994 CB | phenyl | H | CH=CH | $-N(C_2H_5)_2$ | 210–212 |
| 6 | 31,001 CB | phenyl | H | $CH_2CH_2$ | $-N(C_2H_5)_2$ | 140 |
| 7 | 934 CB | cyclohexyl | Cl | $CH_2CH_2$ | $-N(C_2H_5)_2$ | 134 |
| 8 | 31,012 CB | cyclohexyl | Cl | $CH_2CH_2$ | $-N(CH_3)_2$ | 190–191 |
| 9 | 31,016 CB | cyclohexyl | Cl | $CH_2CH_2$ | pyrrolidino | 175–177 |
| 10 | 31,023 CB | cyclohexyl | H | CH=CH | $-N(C_2H_5)_2$ | 171–172 |
| 11 | 31,030 CB | cyclohexyl | F | CH=CH | $-N(C_2H_5)_2$ | 171–172 |

We have discovered that the compounds of formula (I) and their non-toxic acid addition salts have useful pharmacological properties, and specifically have psychostimulant, antispasmodic, hypotensive and analgesic properties. Accordingly, the present invention further consists in a pharmaceutical composition comprising a compound of formula (I) (as hereinbefore defined) or a non-toxic acid addition salt thereof in admixture with a pharmaceutically acceptable excipient.

The psychopharmacological activity of the compounds of the invention was demonstrated by the following tests:

Activity test (Boissier J. R. and Simon P. "Archives Internationales de Pharmacodynamie", 1965, 158, 212).

A mouse was placed in a Plexiglass cage crossed by a plurality of beams of light acting on photoelectric cells. When the mouse moved and thereby interrupted one of the beams, this caused an electrical pulse which was registered on a counter. The measurements were carried out on batches of six treated animals and six control animals for a period of 20 minutes.

Traction test (Courvoisier S., Ducrot R. and Julou L. "Psychotropic Drugs", Elsevier, 1957, p.373)

In this test, a mouse was hung by its front legs on a stretched wire. The animal will normally recover by itself, by gripping with its rear legs within 5 seconds. However, when under the influence of drugs acting on the central nervous system, the animals do not recover successfully.

Balancing test (Boissier J. R., Dumont C. and Ratouis R. "Thérapie", 1960, 15, 1170)

In this test, mice were placed for 1 minute on a horizontal wooden shaft which rotated steadily at 12 r.p.m. The mice will normally counteract this movement using positional and balancing reflexes; if, however, the central nervous system is affected, these reflexes are disturbed and a certain number of animals fall off.

Exploration test (Boissier J. R. and Simon P. "Archives Internationales de Pharmacodynamie", 1964, 147, 372).

This test, using a plank with holes in it, makes it possible to measure objectively the anxiolytic activity of a compound by noting the decrease in the number of holes explored within a given time by a treated mouse in comparison with a control mouse. The animals are used in batches of 10 and are allowed 5 minutes for exploration.

Reserpine test (Rubin B., Malone M. H., Waugh M. H. and Burke J. C., "Journal of Pharmacology and Experimental Therapeutics", 1957, 120, 125)

Reserpine, administered subcutaneously to a mouse in a dose of 5 mg/kg body weight, causes symptoms of severe depression, with absolute fixity, ptosis of the eyelids, hypothermia and catatonia; the simultaneous administration of a substance having anti-depressive properties leads to the progressive total or partial disappearance of this depressed state.

The results obtained from the tests described above are summarized in Table II; the figures given in this Table show the value of the median effective dose for each test. The method of administration is indicated by "I.V." for intravenous administration, "I.P." for intraperitoneal administration and "P.O." for oral administration.

Table II

| Compound | Activity | | Traction | | Balancing | | Exploration | | Reserpine |
|---|---|---|---|---|---|---|---|---|---|
| 933 CB | 25 | I.P. | 50 I.P. | | 30 | I.P. | 25 I.P. | | 75 I.P. |
|  | 100 | P.O. | 100 P.O. | | 50 | P.O. | 25 P.O. | | 100 P.O. |
| 31004 CB | 12.5 | I.P. | >100 I.P. | | 100 | I.P. | 60 I.P. | | — |
| 31013 CB | 50 | I.P. | — | | — | | 50 I.P. | | — |
| 31015 CB | 20 | I.P. | 50 I.P. | | 50 | I.P. | 25 I.P. | | 50 I.P. |
| 994 CB | 100 | I.P. | 100 I.P. | | 50 | I.P. | 50 I.P. | | 50 I.P. |
|  |  |  |  | |  | | 50 P.O. | | 50 P.O. |
| 31001 CB | 50 | I.P. | 100 I.P. | | 100 | I.P. | — | | — |
| 934 CB | 30 | I.P. | — | | 12.5 | I.P. | 20 I.P. | | 50 I.P. |
| 31012 CB | 50 | I.P. | 100 I.P. | | 100 | I.P. | 50 I.P. | | — |
| 31016 CB | 12.5 | I.P. | — | | — | | 20 I.P. | | 50 I.P. |
| 31023 CB | 25 | I.P. | 25 I.P. | | 30 | I.P. | — | | — |
| 31030 | 100 | I.P. | 50 I.P. | | 25 | I.P. | $\geq$ 50 I.P. | | — |

Further experiments relating to the anticataleptic and antispasmodic activity were carried out.

The anticataleptic activity was examined using the prochlorperazine test described by Boissier J. R. and Simon P. ("Thérapie" (1963), 18, 1257). Prochlorperazine, when administered intraperitoneally in a dose of 25 mg/kg to a rat, causes a state of catalepsy which is particularly characterized by the crossing of the homolateral legs: this criterion is used to assess the anticataleptic activity of the compounds of the present invention. For each test there were used 5 control and 5 rats treated with different doses of the compound tested. Using compounds 933 CB and 994 CB, respectively, the effective dose by the intraperitoneal route was 25 mg/kg and per os was 30 mg/kg. The antidepressant activity was assessed using two tests:

Reserpine-induced ulcer in the rat (Blackman J. G. and Campion D. S., "British Journal of Pharmacology", 1959, 14, 112–116)

The administration of reserpine (by the intraperitoneal route in an amount of 5 mg/kg) causes a rat to develop gastric ulcers at the end of from 10 to 20 hours. Antidepressants of the imipramine type prevent the formation of the ulcers or decrease their incidence or seriousness. In this test, the effective dose is, by way of example, when using compound 933 CB 25 mg/kg by the intraperitoneal route and 50 mg/kg by the oral route, and, when using compound 994 CB, 50 mg/kg by the intraperitoneal route and 100 mg/kg by the oral route.

Electroencephalographic study (Schmitt H. and Schmitt H., "Therapie", 1966, 3, 675–684)

Electrical stimulation of the dorsal hippocampus (6 volts; 30 cycles per second; 5 seconds, extent: 1.5 milliseconds) causes electrical discharges in the rabbit which continue for several seconds after cessation of electrical stimulation. These discharges last from 15 to 19 seconds in a normal animal. When the rabbit is under the influence of an antidepressant drug, these discharges last much longer. The experiment was carried out on batches of six conscious rabbits implanted by the technique of Monnier M. and Gangloff H. ("Atlas of Stereotaxic brain research on the conscious rabbit", Elsevier 1961), the products being administered intraveneously. The discharges were increased by 60% when the rabbits were treated with compound 933 CB and by 20 % when the rabbits were treated with compound 994 CB.

The antispasmodic activity of the compounds of the invention was also studied on the isolated rat duodenum, kept alive in an aerated tyrode bath at 37° C. Spasms were induced by the administration of barium chloride in an amount of 100 μg/liter. The compounds of the invention were added, at various concentrations, to the tyrode bath 3 minutes before the addition of the spasmogenic agent and the concentration determined of each which reduced by 50% the extent of the contraction caused by this agent. The results using various compounds according to the present invention are given in Table III.

TABLE III

| Compound | 50% effective concentration (μg/liter) |
|---|---|
| 933 CB | 0.6 to 1 |
| 31004 CB | 1 to 3 |
| 31015 CB | 1 to 3 |
| 994 CB | 3 |
| 31001 CB | 1 |
| 934 CB | 0.6 |
| 31012 CB | 3 |
| 31016 CB | 0.6 to 1 |
| Papaverine hydrochloride | 3 |

In addition, compounds of formula I (as hereinbefore defined) have substantial analgesic properties.

The toxicity of the compounds of the invention is generally low, as may be seen from Table IV, which gives the $LD_{50}$ in mg/kg in mice for some of the compounds of the invention.

TABLE IV

| | $LD_{50}$ | |
|---|---|---|
| Compound | I.P. mg/kg | Orally mg/kg |
| 933 CB | 125 | >1075 |
| 31004 CB | 125 | >750 |
| 31013 CB | 500 | >750 |
| 31015 CB | 62.5 | >750 |
| 934 CB | 125 to 250 | >750 |
| 31012 CB | 250 to 300 | >750 |
| 31016 CB | 50 to 100 | >750 |

The compounds of the invention have been successfully used clinically to treat adynamic and depressive states, such as melancholia, reactive depressions and manic-depressive psychosis.

The compounds of formula (I) may be formulated with physiologically acceptable solid or liquid vehicles.

Where the vehicle is a solid, the compositions of the invention may comprise conventional solid dosage units such as powders, compressed tablets, granules or dragees, or the vehicle may be contained in a capsule, especially a gelatin capsule, or may comprise a suppository base. The vehicle may comprise one or more diluents, perfumes, solubilizing agents, lubricants, binders, surface active agents or disintegrating agents. The vehicle may also comprise one or more coating or encapsulating substances.

The compounds of formula (I) may be formulated as powders in association with a finely divided solid vehicle. In compressed tablets the compounds may be formulated in association with a compressible solid vehicle which can release the compounds after the tablets have been administered. Powders and compressed tablets may contain from 1 to 90% by weight of the compound of formula (I). Examples of such solid vehicles are: magnesium carbonate, magnesium stearate; talc, sucrose; glucose; lactose; pectin; dextrin; starch; gelatin; gum tragacanth; methylcellulose; the sodium salt of carboxymethyl cellulose; low melting point waxes, cocoa butter and semi-synthetic glycerides.

Where the vehicle is a liquid the compositions of the invention may, for example, take the form of an injectible solution, suspension or emulsion comprising a compound of the invention together with sterile pyrogenfree water or an injectible oil. The vehicle may, for example, be a suspension or emulsion containing as one component an aqueous solution of polyethylene glycol or polypropylene glycol and as the other component an oil, preferably olive oil.

Alternatively, where the vehicle is a liquid the composition of the invention may comprise a compound of formula (I) together with a carrier liquid and one or more pharmaceutical adjuvants such as preservatives, flavouring agents, buffering agents, colouring agents, thickening agents, sweetening agents or suspending agents. The composition may take the form of a syrup, an elixir or a linctus or may take the form of a solution or suspension of the compound of formula (I) in a carrier liquid contained in a capsule, especially a soft gelatin capsule. Aqueous suspensions for oral use may comprise thickening agents and suspending agents, for example natural or synthetic gums or resins such as gum arabic; ion-exchange resins; methylcellulose; or carboxymethylcellulose.

The compounds of the present invention are preferably formulated for oral administration or for injection. The compounds of the invention are also suitable for rectal administration. For oral administration, compressed tablets, each containing from 20 to 500 mg of active ingredient are recommended and for injection, ampoules each containing from 10 to 500 mg of active ingredient are recommended. Good results were obtained, especially for compound 933 CB, when administering from 2 to 10 compressed tablets, each containing 100 mg of the compound, daily or when administering from 1 to 5 injectible ampoules each containing 100 mg of the compound.

Examples of suitable formulations are as follows:

| Compressed tablets: | |
|---|---|
| 933 CB, hydrochloride | 100 mg. |
| Lactose | 200 mg |
| Potassium polymethacrylate | 30 mg. |
| Magnesium stearate | 10 mg |
| Injectible ampoules: | |
| 933 CB, hydrochloride | 100 mg |
| Distilled water, q.s.f. | 5 ml. |
| Capsules: | |
| 933 CB, hydrochloride | 10 mg |

| -continued | |
|---|---|
| Talc q.s.f. | 105 mg |
| Suppositories: | |
| 933 CB, hydrochloride | 15 mg |
| Mixture of mono-, di- and triglycerides of saturated fatty acids q.s.f. | 3 g |

A clinical evaluation of 933 CB was carried out using a sample of 30 severely depressed hospital patients who were considering suicide or in some cases had attempted it. The sample contained 13 cases of nervous depression, 10 cases of reactional depression, seven cases of psychotic depression and three cases of severe melancholia. A clear favourable action on the depressive thymine occurred in 21 of the patients. Several cases where a favourable response was noted had previously been treated with tricyclic antidepressants without success. The action was rapid, an improvement being noted in less than a week in 13 of the patients. The daily dose of the compound administered to each patient varied from 20 to 200 mg, the most favourable results being obtained with a dose of 40 to 60 mg.

I claim:

1. A method of treating adynamic and depressive states in a patient suffering from said states which comprises administering an anti-depressive amount of a compound of the formula:

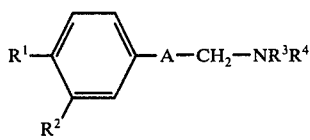
(I)

in which $R^2$ is selected from the group consisting of a hydrogen atom and a halogen atom; $R^1$ is selected form the group consisting of a cyclohexyl group and phenyl group; and is a cyclohexyl group when $R^2$ is a halogen atom; A is selected from the group consisting of $CH_2CH_2$ and $CH=CH$ groups; and $NR^3R^4$ is selected from the group consisting of an alkylamino group, a dialkylamino group and a heterocyclic group selected from the group consisting of pyrrolidino, morpholino, thiomorpholino, 2,6-dimethylmorpholino, piperidino, 4-methylpiperidino, piperazino, 4-($\beta$-hydroxyethyl)-piperazino, 4-methylpiperazino and azepino groups; and acid addition salts of said compounds.

2. The method of claim 1 wherein the compound is 3-chloro-4-cyclohexyl-1-(3-diethylamino-propen-1-yl)-benzene and its acid addition salts.

3. The method of claim 1 wherein the compound is 3-chloro-4-cyclohexyl-1-(3-dimethylamino-propen-1-yl)-benzene and its acid addition salts.

4. The method of claim 1 wherein the compound is 3-chloro-4-cyclohexyl-1-(3-morpholinopropen-1-yl)-benzene and its acid addition salts.

5. The method of claim 1 wherein the compound is 3-chloro-4-cyclohexyl-1-(3-pyrrolidino-propen-1-yl)-benzene and its acid addition salts.

6. The method of claim 1 wherein the compound is 4-(3-diethylamino-propen-1-yl)-biphenyl and its acid addition salts.

7. The method of claim 1 wherein the compound is 4-(3-diethylamino-propyl)-biphenyl and its acid addition salts.

8. The method of claim 1 wherein the compound is 3-chloro-4-cyclohexyl-1-(3-diethylamino-propyl)-benzene and its acid addition salts.

9. The method of claim 1 wherein the compound is 3-chloro-4-cyclohexyl-1-(3-dimethylamino-propyl)-benzene and its acid addition salts.

10. The method of claim 1 wherein the compound is 3-chloro-4-cyclohexyl-1-(3-pyrrolidino-propyl)-benzene and its acid addition salts.

11. The method of claim 1 wherein the compound is 4-cyclohexyl-1-(3-diethylamino-propen-1-yl)-benzene and its acid addition salts.

12. The method of claim 1 wherein the compound is 3-fluoro-4-cyclohexyl-1-(3-diethylamino-propen-1-yl)-benzene and its acid addition salts.

* * * * *